United States Patent [19]

Guest et al.

[11] 4,252,976
[45] Feb. 24, 1981

[54] PROCESS FOR THE PREPARATION OF THIOPHENES

[75] Inventors: Angela W. Guest, Little Bookham; Andrew W. Taylor, Dorking; Robert Ramage, Altrincham, all of England

[73] Assignee: Beecham Group Limited, Fed. Rep. of Germany

[21] Appl. No.: 926,727

[22] Filed: Jul. 21, 1978

[30] Foreign Application Priority Data

Jul. 23, 1977 [GB] United Kingdom ............... 31008/77

[51] Int. Cl.$^3$ .......................................... C07D 333/24
[52] U.S. Cl. .................................. 549/79; 260/465.4; 560/192; 549/74; 549/76; 549/77; 560/219
[58] Field of Search .................... 260/329 R, 332.3 R; 549/79, 74, 76, 77

[56] References Cited

PUBLICATIONS

Hartough, Howard D. "Thiophene and its Derivatives", Interscience Publ. (1952), pp. 74–76, 82–85.
Houben–Weyl, "Methoden der Organischen Chemie", vol. 9 (1955), p. 7.
Janssen, Matthijs J., "Organosulfur Chemistry", Interscience Publ. (1968), pp. 136–141.

Primary Examiner—Natalie Trousof
Assistant Examiner—L. Hendriksen
Attorney, Agent, or Firm—Jacobs & Jacobs

[57] ABSTRACT

A process for the preparation of 3-substituted thiophenes which involves cyclization of a novel intermediate, avoids the use of previously employed expensive starting materials. The thiophenes are useful for the preparation of penicillins and cephalosporins.

The process is for the preparation of a thiophene of formula (I):

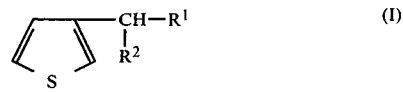

where $R^1$ represents a carboxylic acid group, or an ester or amide thereof or a nitrile group; $R^2$ represents a group suitable for use as an α-substituent in the side-chain of a penicillin or cephalosporin; which comprises treating a compound of formula (II):

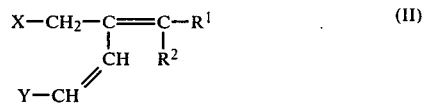

wherein X represents halogen or optionally functionalized hydroxyl, Y represents halogen, hydroxyl, or alkoxy; with a source of nucleophilic sulphur under basic conditions.

9 Claims, No Drawings

PROCESS FOR THE PREPARATION OF THIOPHENES

This invention relates to a chemical process for the preparation of 3-substituted thiophenes, which are useful as intermediates in the production of penicillins and cephalosporins.

A number of important penicillins and cephalosporins having a 3-thienyl group in the side-chain are well known. For example our British Pat. No: 1,004,670 describes the penicillin 'ticarcillin', viz α-carboxy-3-thienylmethyl-penicillin, whilst esters of that compound are disclosed in our British Pat. Nos. 1,125,557 and 1,133,886. The 6α-methoxy substituted derivative of ticarcillin in disclosed in W. German Offenlegungsschrift No. 2,600,866.

α-Carboxy-3-thienylmethylcephalosporin is disclosed as an antibacterial agent in U.K. Pat. No. 1,193,302.

The most widely used method of preparation of this type of penicillin and cephalosporin is the process disclosed in British Pat. No. 1,125,557 wherein the penicillins are prepared from a 3-thienylmalonic ester itself synthesised from 3-thienylacetonitrile. The 3-thienylacetonitrile was prepared from 3-methylthiophene by the method of Campaigne et al (J.Amer.-Chem.Soc. 1948, 70, 1553) which involves reaction with N-bromo-succinimide and treatment of the resulting 3-bromomethylthiophene with sodium cyanide. However, this bromination gives the desired bromo-derivative in low yield and the 3-methylthiophene starting material is unduly expensive, with the result that the final penicillin or cephalosporin is considerably more expensive than other penicillin and cephalosporin derivatives.

We have now devised a process for the preparation of 3-substituted thiophenes which involves cyclization of a novel intermediate to form the thiophene moiety. The process is applicable to a wide variety of 3-substituents.

Accordingly the present invention provides a process for the preparation of a thiophene of formula (I):

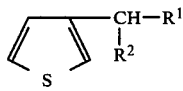

wherein $R^1$ represents a carboxylic acid group or an ester or amide derivative thereof or a nitrile (—CN) group; and $R^2$ represents hydrogen, a hydrocarbon or heterocyclic group, a carboxylic acid group or an ester or amide derivative thereof, or an acyl, nitrile, isonitrile (—NC) or optionally substituted imine group of formula —CH=NZ or —N=CHZ (where Z represents hydrogen, alkyl or aryl), or a sulphonyl, —$SR^a$, sulphoxide —$SO_2.R^a$ or sulphonate —$SO.OR^a$ group wherein $R^a$ represents $C_{1-6}$ alkyl, or aryl, which process comprises treating a compound of formula (II):

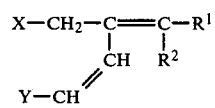

wherein $R^1$ and $R^2$ are as defined with respect to formula (I) above; X represents a halogen atom, a hydroxyl group or a functionalized hydroxyl group; and Y represents a halogen atom or a hydroxyl or alkoxy group; with a source of nucleophilic sulphur under basic conditions.

This cyclization process may be carried out in a wide range of solvents subject to the solubility of the source of nucleophilic sulphur. It is often convenient to use a polar solvent, preferably a water—miscible solvent such as, for example, tetrahydrofuran, acetone, dimethylformamide, dimethylsulphoxide, hexamethylphosphoramide, acetonitrile, dimethoxyethane, dioxan, or an alcohol such as methanol, ethanol, propanol, butanol, in particular ethanol. Preferred solvents include tetrahydrofuran and acetone. An organic solvent such as methylene dichloride may also be employed. The reaction may be carried out at ambient to elevated temperature depending on the particular reagents used and the values of X, Y, $R^1$ and $R^2$. For example suitable temperatures for the process are from −20° C. to 100° C., preferably 10° to 50° C.

It is necessary to use a source of nuleophilic sulphur in the process of this invention. It is thought that the initial step in the process is nucleophilic displacement of the group Y in compound (II) by a sulphur moiety, and the ability to displace a group Y is the criterion for choosing a compound suitable for providing the source of nucleophilic sulphur for the process of this invention. Basic conditions are required for the subsequent step, which is thought likely to be formation of an intermediate of formula (III):

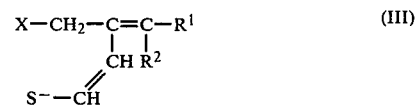

which then undergoes displacement of the group X by internal nucleophilic attack by the sulphide, S⁻, in structure (III), an hence cyclisation to give compound (I).

Although it is usually most convenient to have the reaction under basic conditions when the source of nucleophilic sulphur is added to the compound (II), it is also possible to carry out the reaction in two steps, that is by firstly treating compound (II) with a source of nucleophilic sulphur and then subsequently completing the cyclisation reaction by addition of a base.

One suitable source of nucleophilic sulphur is for example the bisulphide ion, HS⁻.

The bisulphide ion for the process of this invention may be provided by using a salt of this ion, preferably an alkali metal salt for example sodium bisulphide NaSH, which may be prepared, optionally in situ in the reaction, from sodium sulphide $Na_2S$ and sodium bicarbonate. An alternative, and preferred, source of the bisulphide ion comprises hydrogen sulphide and a base, which again produces HS⁻ in situ.

This combination of reagents has the advantage that the base employed can be the same as that used for the cyclisation process itself.

Suitable bases which may be employed to provide the basic conditions for the process of this invention include inorganic bases, such as alkali metal hydroxides, preferably potassium hydroxide, and alkali metal bicarbonates preferably sodium bicarbonate and organic basis such as substituted amines for example tri($C_{1-6}$)alkylamines such as trimethylamine or triethylamine.

The bisulphide ion may also be generated in situ from sulphurated sodium borohydride, $NaBH_2S_3$.

In some cases it is possible to employ a compound for providing the source of nucleophilic sulphur, which compound is also capable of providing the basic conditions for the cyclization step. Alkali metal bisulphides, especially sodium bisulphide, are suitable such compounds. Thus reaction of compound (II) with an alkali metal bisulphide produces an intermediate of formula (IV):

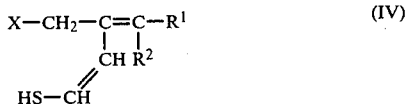

(IV)

Addition of further bisulphide (or presence of excess initially) removes a proton to give structure (III) above which then cyclises.

Another way of providing the basic conditions required for the process is to produce the intermediate ion of formula (III) directly which can then act as its own base for cyclisation. This may be achieved for example by treating compound (II) with an alkali metal sulphide, in particular sodium sulphide $Na_2S$. Because the sulphur ion in such a compound has a double negative charge, $S^{2-}$, the intermediate formed after nucleophilic attack on compound (II), is structure (III) rather than structure (IV). No further base need then be present to complete the cyclisation. This reaction is still under basic conditions by virtue of the presence of the ion (III) itself, or excess of the alkali metal sulphide; if the reaction medium became neutral or acidic, the sulphide ion in structure (III) would be protonated and the cyclization would not proceed.

The compounds of formula (II) are novel compounds and constitute a further aspect of this invention.

In formula (II) the group X should be readily displaced by nucleophilic attack by sulphide ions. Such groups include chlorine, bromine, hydroxyl, arylsulphonyloxy such as benzenesulphonyloxy, p-toluenesulphonyloxy, or p-nitrosulphonyloxy, alkylsulphonyloxy such as methyanesulphonyloxy or $C_{1-6}$ alkanoyloxy such as acetoxy, propionoxy or butyroxy.

The group Y may be, for example, chlorine, bromine, hydroxy or $C_{1-6}$ alkoxy such as methoxy, ethoxy, or propoxy. Preferably both X and Y are halogen, especially chlorine.

The radicals $R^1$ and $R^2$ in compound (II) are chosen according to the requirements of the compound (I). For the preparation of penicillin and cephalosporin derivatives the group $R^1$ should be a carboxylic acid group or a group which may be converted to a carboxylic acid group or a functional derivative thereof for acylation the amino group of the penicillin or cephalosporin nucleus. The $R^2$ group is chosen to provide the required α-substituent, or a precursor thereof, for the side chain of a penicillin or cephalosporin.

The radical $R^1$ may be an ester group $—CO_2R^3$ wherein $R^3$ is an alkyl, cycloalkyl, alkenyl, alkynyl, aryl or heterocyclic group, any of which may be substituted. Suitable such $R^3$ groups include:

(a) alkyl especially $C_{1-6}$ alkyl such as methyl, ethyl, n- and iso-propyl, n-, sec-, iso- and tert-butyl, and pentyl;

(b) substituted $C_{1-6}$ alkyl wherein the substituent is at least one of: chloro, bromo, fluoro, nitro, carbo($C_{1-6}$ alkoxy), $C_{1-6}$ alkanoyl, $C_{1-6}$ alkoxy, cyano, $C_{1-6}$ alkylmercapto, $C_{1-6}$ alkylsulfinyl, $C_{1-6}$ alkylsulphonyl, 1-indanyl, 2-indanyl, furyl, pyridyl, 4-imidazolyl, phthalimido, azetidino, aziridino, pyrrolidino, piperidino, morpholino, thiomorpholino, N-($C_{1-6}$ alkyl)-piperazino, pyrrolo, imidazolo, 2-imidazolino, 2,5-dimethylpyrrolidino, 1,4,5,6-tetrahydropyrimidino, 4-methylpiperidino, 2,6-dimethylpiperidino, alkylamino, dialkylamino, alkanoylamino, N-alkylanilino, or substituted N-alkylanilino wherein the substituent is chloro, bromo, $C_{1-6}$ alkyl or $C_{1-6}$ alkoxy;

(c) cycloalkyl and ($C_{1-6}$ alkyl) substituted cycloalkyl having from 3 to 7 carbon atoms in the cycloalkyl moiety;

(d) alkenyl having up to 8 carbon atoms;

(e) alkynyl having up to 8 carbon atoms;

(f) phenyl and substituted phenyl wherein the substituent is at least one of chloro, bromo, fluoro, $C_{1-6}$ alkoxy, $C_{1-6}$ alkanoyl, carbo-($C_{1-6}$) alkoxy, nitro, or di($C_{1-6}$) alkyl amino;

(g) benzyl or substituted benzyl wherein the substituent is chloro, bromo, fluoro, $C_{1-6}$ alkyl, $C_{1-6}$ alkoxy, $C_{1-6}$ alkanoyl, carbo-($C_{1-6}$)-alkoxy, nitro, or di($C_{1-6}$-alkyl)amino;

(h) a 5- or 6-membered hereocyclic group containing one or more sulphur and/or nitrogen and/or oxygen atoms in the ring optionally fused to a second 5- and 6-membered hydrocarbyl or heterocyclic ring and which may be substituted with an alkyl group having 1 to 3 carbon atoms, for example thienyl, furyl quinolyl, methyl-substituted quinolyl, phenazinyl, pyridyl, methylpyridyl, phthalidyl, indanyl.

Preferred groups for $R^3$ include $C_{1-6}$ alkyl, benzyl, phthalidyl, indanyl, phenyl, mono-, di-, and tri-($C_1C_6$)-alkyl substituted phenyl such as o-, m or p methylphenyl, ethylphenyl, n- or iso-propylphenyl, n-, sec-, iso- or butylphenyl.

Suitable groups $R^2$ include hydrogen, $C_{1-6}$ alkyl, such as methyl, ethyl, propyl, or butyl, benzyl, phenyl, alkylphenyl, naphthyl, a 5- or 6-membered heterocyclic group containing one or more sulphur and/or nitrogen and/or oxygen atoms in the ring and which may be substituted by an alkyl group having from 1 to 3 carbon atoms, for example thienyl imidazolyl, thiadiazolyl, isoxazolyl, methylisoxazolyl, tetrazolyl, methyltetrazolyl, pyrimidinyl, pyridyl, pyrazinyl, pyrrolidyl, piperidyl, morpholinyl, thiazinyl, furyl, or quinolyl; a carboxylic acid group, a carboxylic ester group $—CO_2R^3$ as defined above, or a $C_{1-6}$ alkanoyl group. When both groups $R^1$ and $R^2$ are ester radicals they may together form a cyclic ester group, for example iso-propylidine of formula:

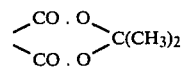

For the preparation of α-carboxy-3-thienyl penicillins and cephalosporins, $R^1$ and $R^2$ may conveniently both be carboxylic acid or ester radicals. It is convenient to prepare a diester compound of formula (I), i.e. where $R^1$ and $R^2$ both represent a group $—CO_2R^3$, and then half-saponify in order to produce the compound (I) wherein one of $R^1$ and $R^2$ is a carboxylic acid group, suitable for coupling to the penicillin or cephalosporin nucleus.

Similarly for the preparation of an α-ester of an α-carboxy-3-thienyl penicillin or caphalosporin, the group $R^3$ may be chosen according to the eventual penicillin or cephalosporin required.

The compound of formula (II) above may be prepared by a process which comprises condensing a compound of formula (V):

(V)

wherein X and Y are as defined above with respect to formula (II); with a compound of formula (VI):

(VI)

wherein $R^1$ and $R^2$ are as defined above with respect to formula (I); under mild condensation conditions; and subsequently, if required, converting one group X or Y to a different such group.

The conditions used for this condensation reaction should be sufficiently mild to prevent or minimise self-condensation or other unwanted reaction of the compound (II), and the conditions and reagents employed for the reaction depend on the nature of the groups $R^1$ and $R^2$. In general, the more electron-withdrawing are the groups $R^1$ and $R^2$ then the more activated is the methylene group in compound (VI) and milder conditions may be employed.

When both the groups $R^1$ and $R^2$ are selected from a carboxylic acid group, a carboxylic ester group or an activated acyl group (for example in the form of a silyl enol ether), then the condensation of compound (V) with compound (VI) may conveniently be carried out in the presence of titanium tetrachloride and an organic nitrogen-containing base containing no acidic proton, for example pyridine. Suitable solvents for such a reaction are chlorinated hydrocarbon solvents, preferably carbon tetrachloride, optionally in the presence of a co-solvent such as tetrahydrofuran, dioxan or a polar aprotic solvent. The condensation is conveniently carried out at low to ambient temperature, preferably from 0° C. to 25° C.

Many compounds of the general formula (V) are known in the literature and may be prepared by a process which comprises reacting a compound of formula (VII):

(VII)

wherein X is as defined with respect to formula (II) above and T represents halogen; with acetylene in the presence of an aluminium halide, Al $U_3$, wherein U represents halogen which may be the same as or different from T; to produce a compound of formula (VIII):

(VIII)

and subsequently, if required replacing the group U by a group Y and optionally converting the group X into a different such group.

This reaction may be carried out using conventional conditions known in the literature, for example as described by Naito et al, J. Antibiot (Tokyo) Ser A 20 (2), 77–86 (1967) or by Benson and Pohland, J. Org. Chem. 29, 385.

The compounds of formula (I) in which one of the groups $R^1$ and $R^2$ represents a carboxylic acid function may be converted to a penicillin or cephalosporin by an method known per se, for example as described in British Pat. Nos. 1,004,670, 1,125,557, 1,333,886, 1,193,302, W. German OLS No. 2,600,866.

The following Examples illustrate this invention.

EXAMPLE 1

Preparation of 1,4-dichlorobut-3-en-2-one

Aluminium chloride (39.9 g, 0.3 mol) in carbon tetrachloride (150 ml) was treated with chloroacetylchloride (22.3 ml, 0.3 mol) while acetylene was passed through the reaction mixture. Acetylene addition was continued with stirring for 3 hours. Water was added to the reaction mixture, which was extracted with ether. The combined ether extracts were washed with saturated brine, N sodium bicarbonate solution, saturated brine, dried and evaporated to give the crude title compound (34.1 g, 82%) as a mixture of cis and trans isomers. Cis isomer $\delta$ (CDCl$_3$) 4.32 (2H, s, CH$_2$), 6.66 (1H, d, 8 Hz, —CH=), 6.88 (1H, d, J 8 Hz, —CH=), trans isomer $\delta$ (CDCl$_3$) 4.22 (2H, s, CH$_2$), 6.82 (1H, d, J 14 Hz, CH=), 7.52 (1H, d, J 14 Hz, CH=). $\nu_{max}$ (film) 1580, 1690 cm$^{-1}$.

EXAMPLE 2

Preparation of trans 1,4-dichlorobut-3-en-2-one.

Aluminium chloride (79.8 g, 0.6 mol) in methylene dichloride (300 ml) was treated with stirring with chloroacetyl chloride (44.6 ml, 0.56 mol). Acetylene (ca 1.2 mol) was passed throught the reaction mixture with stirring for three hours at a flow rate of 150 ml/min. The reaction solution was slowly treated with ice-water (200 ml), and the mixture extracted with methylene dichloride (200 ml, 2×100 ml). The combined extracts are washed with brine (2×50 ml) and saturated sodium bicarbonate (50 ml), dried (Na$_2$SO$_4$) and evaporated to give the title product in 74% yield, b.p. 71°–74°/10 mm. $\delta$ (CDCl$_3$) 4.22 (2H, s, CH$_2$), 6.82 (1H, d, J 14 Hz, CH=), 7.52 (1H, d, J 14 Hz, CH=), $\nu_{max}$ (film) 1580, 1690 cm$^{-1}$.

EXAMPLE 3

Preparation of cis 1,4-dichlorobut-3-en-2-one.

The proceedure described in Example 2 was repeated, but with a shorter reaction time (ninety minutes) to give a 50:50 mixture of cis and trans isomers. Chromatography (silica gel; 10% ethyl acetate in 60–80 petrol ether afforded the slower moving cis isomer (29% yeld). $\delta$ (CDCl$_3$) 4.35 (2H, s, CH$_2$), 6.67 (1H, d, J 8 Hz, CH=), 6.90 (1H, d, J 8 Hz, CH=). $\lambda_{max}$ (ethanol) 239 nm ($\epsilon_m$=8,450). $\nu_{max}$ (film) 1595, 1690, 1710 cm$^{-1}$. Found: M$^+$138. C$_4$H$_4$Cl$_2$O requires M, 138.

EXAMPLE 4

Preparation of ethyl 4-trans-2-ethoxycarbonyl-5-chloro-3-chloromethyl penta-2,4-dienoate.

Titanium tetrachloride (10 ml., 0.1 mol) in CCl$_4$ (10 ml) was added to tetrahydrofuran (25 ml) at 0°. A premix of trans 1,4-dichlorobut-3-en-2-one (5.6 g, 0.04 mol) and diethyl malonate (6.45 g., 0.04 mol) was added in tetrahydofuran (20 ml). Over 20 minutes, pyridine (13.0 ml., 0.16 mol) in tetrahydrofuran (10 ml) was added. The reaction mixture was stirred for three hours at room temperature, diluted with water (100 ml) and extracted with MDC (50 ml., 2×25 ml). The combined extracts were washed with brine (2×20 ml), N sodium bicarbonate solution (20 ml), dried (Na$_2$SO$_4$) and evaporated to give the title product (61% yield). δ (CDCl$_3$)1.37 (6H, t, J 7 Hz, CH$_3$), 4.39 (4H, q, J 7 Hz, OCH$_2$), 4.62 (2H, s, CH$_2$), 7.12 (2H, s, CH=CH). $\nu_{max}$ (film) 1610, 1720 cm$^{-1}$. C$_{11}$H$_{14}$O$_4$Cl$_2$ requires M, 280.0269. Found: M+, 280.0256.

EXAMPLE 5

Preparation of ethyl 4-cis-2-ethoxycarbonyl-5-chloro-3-chloromethyl penta-2,4-dienoate cis 1,4-Dichlorobut-3-en-2-one was condensed with diethyl malonate under the conditions described in Example 4, to give the title product (67% yield). δ (CDCl$_3$) 1.28 (3H, t, J 7 Hz, CH$_3$), 1.33 (3H, t, J 7 Hz, CH$_3$), 4.26 (2H, q, J 7 Hz, OCH$_2$), 4.33 (2H, q, J 7 Hz, OCH$_2$), 4.67 (2H, s, CH$_2$), 6.35 (1H, d, J 8 Hz, CH=), 6.70 (1H, d, J 8 Hz, CH=). $\lambda_{max}$ (ethanol) 269 nm (vm=6,000). $\nu_{max}$ (film) 1610, 1720 cm$^{-1}$.

EXAMPLE 6

Preparation of methyl 4-trans-2-methoxycarbonyl-5-chloro-3-chloromethyl penta-2,4-dienoate.

Titanium tetrachloride (10 ml., 0.1 mol) in carbon tetrachloride (25 ml) was added to tetrahydrofuran (THF) (250 ml) at 0° C. A premix of trans-1,4-dichlorobut-3-en-2-one (5.6 g., 0.04 mol) and diethylmalonate (4.2 ml., 0.037 mol) in THF (20 ml) was added. Pyridine (13.0 g., 0.16 mol) in THF (80 ml) was added over 20 mins. The reaction mixture was stirred at room temperature for 16 hours, diluted with water, and extracted with ether. The ether extracts were washed with brine, sodium bicarbonate solution, and brine. Drying and evaporation gave the title compound (7.72 g., 77%). Recrystallisation from ether:petrol gave large prisms, m.p. 56°, $\nu_{max}$ (film) 1730, 1610 cm$^{-1}$, δ (CDCl$_3$) 3.85 (6H, s, 2×CH$_3$), 4.60 (2H, s, CH$_2$), 7.03 (2H, s, CH=CH). Found: C, 42.9; H, 4.0; Cl, 28.0% C$_9$H$_{10}$O$_4$Cl$_2$ requires C, 42.7; H, 4.0; Cl, 28.0%.

EXAMPLE 7

Preparation of methyl 4-trans-2-methoxycarbonyl-5-chloromethyl penta-2,4-dienoate Titanium tetrachloride (0.5 ml, 5.0 mol) in carbon tetrachloride (1.5 ml) was added to THF (10 ml) at 0° C. A premix of trans-1,4-dichlorobut-3-en-2-one (0.28 g., 2.0 mol) and diethyl malonate (0.22 ml., 2.0 mol) in THF (2 ml) was added. Over 5 minutes, pyridine (0.32 ml., 4.0 mol) in THF (4 ml) was added. Calcium carbonate (0.4 g., 4.0 mol) was added and the reaction mixture stirred at room temperature for 3 hours, diluted with water and extracted with ether. The ether extracts were washed with brine, sodium bicarbonate solution, brine; dried, treated with charcoal and evaporated to give the title compound in 69% yield, purified as in Example 6 (Spectroscopic data as in Example 6).

EXAMPLE 8

Preparation of benzyl 4-trans-2-benzyloxycarbonyl-5-chloro-3-chloromethyl penta-2,4-dienoate.

Trans-1,4-dichlorobut-3-en-2-one (2.8 g., 20.0 mmol) and dibenzyl malonate (5.7 g., 20.0 mmol) were condensed as in Example 6 using the TiCl$_4$/pyridine method, thus affording the title compound in 46% yield. Recrystallization from ethanol gave prisms, m.p. 45°-6°, $\nu_{max}$ (CH$_2$Cl$_2$) 1730, 1610 cm$^{-1}$, δ (CDCl$_3$) 4.50 (2H, s, ClCH$_2$), 5.24 (4H, s, 2×PhCH$_2$-), 7.00 (2H, s, CH=CH), 7.36 (10H, s, arylprotons), $\lambda_{max}$ (EtoH) 277 nm ($\epsilon$22,100).

EXAMPLE 9

Preparation of 4-cis 2-carboxy-5-chloro-3-chloromethyl penta-2,4-dienoic acid

Titanium tetrachloride (2.5 ml., 25 mmol) in carbon tetrachloride (7.5 ml) was added to THF (60 ml) at 0° C. Malonic acid (1.0 g., 10 mmol) and trans 1,4-dichlorobut-3-en-2-one (1,4 g., 10 mmol) in THF (10 ml) was added. Pyridine (3.3 ml., 40 mmol) in THF (10 ml) was added dropwise over fifteen minutes at 0° C. The reaction mixture was stirred at room temperature for three hours, diluted with water (50 ml) and extracted with ether (50 ml., 2×25 ml). The extracts were washed with brine, N sodium bicarbonate solution, brine, dried (Na$_2$SO$_4$) and evaporated to give the title product (0.35 g., 12%). ≠ (CDCl$_3$) 5.00 (2H, s, CH$_2$), 6.91 (1H, d, J 5 Hz, CH=), 8.01 (1H, d, J 5 Hz, CH=), 9.68 (2H, s, —OH). $\nu_{max}$ (CHCl$_3$) 1720 cm$^{-1}$.

EXAMPLE 10

Preparation of ethyl 4-trans-2-cyano-5-chloro-3-chloromethyl penta-2,4-dienoate

Titanium tetrachloride (0.25 ml, 2.5 mmol) in CCl$_4$ (1.5 ml) was added to THF (10 ml) at 0° C. Trans-1,4-dichlorobut-3-en-2-one (0.28 g, 2.0 mmol) and ethyl cyanoacetate (0.21 g, 1.9 mmol) in THF (2 ml) were added. Pyridine (0.32 ml, 4.0 mmol) in THF (5 ml) was added over 5 minutes, and the mixture stirred for eighteen hours at room temperature. Work up as in example 6 gave the title compound (0.04 g, 8%). The E:Z isomeric mixture possessed δ (CDCl$_3$) 1.37 (3H, t, J 7 Hz, CH$_3$), 4.39 (2H, q, J 7 Hz, CH$_2$) 4.60 (2H, s, CH$_2$), 7.30 (2H, complex, CH=CH); 1.42 (3H, t, J Hz, CH$_3$), 4.43 (2H, q, J 7 Hz, CH$_2$), 4.93 (2H, s, CH$_2$), 7.30 (2H, complex, CH=CH).

EXAMPLE 11

Preparation of methyl 5-chloro-3-chloromethyl penta-2,4-dienoate (cis/trans mixture)

Cis-1,4-dichlorobut-3-en-2-one (0.28 g, 2.0 mmol) in toluene (5 ml) was heated at 90° with carbomethoxymethylene triphenylphosphorane (0.66 g, 2.0 mmol) for 15 hours. Water was added, and extracted with ether. Drying, evaporation and chromatography on silica gave the title compound as a mixture of Δ$_{4,5}$ cis and trans-isomers (0.05 g, 13%), $\nu_{max}$(film) 1720, 1625 cm$^{-1}$; δ (CDCl$_3$) (cis-isomer) 3.60 (3H, s, —CH$_3$), 4.55 (2H, s, —CH$_2$—), 6.23 (1H, s, CHCO$_2$—), 6.37 (1H, d, J 8 Hz, CH=), 7.27 (1H, d, J 8 Hz, CH=); (trans-isomer) 3.60 (3H, s, —CH$_3$), 4.40 (2H, s, —CH$_2$—), 6.03 (1H, s, CHCO$_2$—), 6.85 (1H, d, J 14 Hz, CH=), 7.95 (1H, d, J 14 Hz, Ch=).

EXAMPLE 12

Preparation of methyl 4-trans-5-chloro-3-chloromethyl-penta-2,4-dienoate trans 1,4-Dichlorobut-3-en-2-one(0.56 g, 4.0 mmol) in toluene (10 ml) was stirred with methoxycarbonylmethylenetriphenyl phosphorane (1.32 g, 4.0 mmol) at 90° C. for sixteen hours. Water (50 ml) was added and the mixture extracted with ether (50 ml, 2×25 ml). The extracts were dried (Na$_2$SO$_4$) and evaporated to give the title compound (0.11 g, 14%), spectral details as in Example 11.

EXAMPLE 13

Preparation of diethyl thien-3-ylmalonate

Potassium hydroxide (0.14 g, 2.0 mmol) in ethanol (50 ml) was saturated with hydrogen sulphide at 0° for one hour. To this was added 4-trans ethyl-2-ethoxycarbonyl-5-chloro-3-chloromethylpenta-2,4-dienoate (0.62 g, 2.45 mmol), and addition of hydrogen sulphide was continued for one hour at room temperature. The reaction mixture was stirred for a further four hours. Potassium hydroxide (0.20 g, 2.8 mmol) was added and hydrogen sulphide passed for thirty minutes. The reaction mixture was stirred at room temperature for sixteen hours, diluted with water (50 ml) and extracted with ether (3×50 ml). The extracts were washed with saturated brine, N sodium bicarbonate solution, saturated brine, dried (Na$_2$SO$_4$) and evaporated to give the title compound (78% yield) purified by distillation, b.p. 119°–127°/0.5 mm. δ (CDCl$_3$) 1.27 (6H, t, J 7 Hz, CH$_3$), 4.20 (4H, q, J 7 Hz, OCH$_2$), 4.75 (1H, s, CH), 7.20–7.43 (3H, m, thienyl protons), $v_{max}$(film) 1730 cm$^{-1}$, λ$_{max}$ (ethanol) 234 nm. C$_{11}$H$_{14}$O$_4$S requires M, 242.0649. Found M+, 242.0609.

EXAMPLE 14

Preparation of diethyl thien-3-ylmalonate

Ethyl 4-trans-2-ethoxycarbonyl-5-chloro-3-chloromethyl penta-2,4-dienoate (0.28 g, 1.0 mmol) in THF (5 ml) was treated with solid sodium sulphide nonahydrate (0.24 g, 1.0 mmol) and the mixture stirred at room temperature for sixteen hours. Ether (50 ml) was added; brine washing, drying (Na$_2$SO$_4$), charcoal and evaporation gave the title product (66% yield), spectral details as in Example 13.

EXAMPLE 15

Preparation of diethyl thien-3-ylmalonate

Sodium sulphide (Na$_2$S.9H$_2$O) (12 g, 0.05 mol) was dissolved in water and the volume made up to 35 ml. Sodium bicarbonate (4.2 g, 0.05 mol) was added with stirring. After dissolution, methanol (30 ml) was added. After thirty minutes, sodium carbonate was filtered off, and the solids washed with methanol (15 ml). There is thus obtained a solution of sodium bisulphide (50 mmol) in aqueous methanol.

Ethyl 4-trans-2-ethoxycarbonyl-5-chloro-3-chloromethyl penta-2,4-dienoate (1.4 g, 5 mmol) in methanol (50 ml) was treated at 10° C., dropwise with sodium bisulphide solution (8 ml, 5 mmol). After two hours at room temperature, a further aliquot of sodium bisulphide solution (8 ml, 5 mmol) was added and the mixture stirred overnight. The solution was concentrated (ca 5 ml) and water (50 ml) added. Ether extraction (3×50 ml), brine washing (50 ml) drying (Na$_2$SO$_4$), charcoal and evaporation gave the title product (68% yield), spectral details as in Example 13.

EXAMPLE 16

Preparation of diethyl thien-3-ylmalonate

Ethyl 4-trans-2-ethoxycarbonyl-5-chloro-3-chloromethyl penta-2,4-dienoate (0.28 g, 1.0 mmol) in methylene dichloride (10 ml) at 0°–5° C. was treated with hydrogen sulphide for ten minutes. A solution of triethylamine (0.28 ml, 2.0 mmol) in methylene dichloride (5 ml) was added over five minutes, and the solution stirred at room temperature for forty-five minutes, diluted with methylene dichloride (25 ml), washed with brine (25 ml) dried (Na$_2$SO$_4$) and evaporated to give the title product (62% yield), spectral details as in Example 13.

EXAMPLE 17

Preparation of diethyl thien-3-ylmalonate

Ethyl 4-cis-2-ethoxycarbonyl-5-chloro-3-chloromethyl penta-2,4-dienoate (0.84 g, 3.0 mmol) in tetrahydrofuran (15 ml) was stirred with sodium sulphide nonahydrate (0.72 g, 3.0 mmol) at room temperature for sixteen hours. The reaction mixture was diluted with ether, washed with brine, dried (Na$_2$SO$_4$), treated with charcoal, filtered and evaporated to give the title product (0.18 g, 28%), spectral details as in Example 13.

EXAMPLE 18

Preparation of dimethyl thien-3-ylmalonate

Methyl 4-trans-2-methoxycarbonyl-5-chloro-3-chloromethyl penta-2,4-dienoate (1.25 g., 5.0 mmol.) in THF (15 ml) was stirred for 18 hours with sodium sulphide nonahydrate (1.68 g., 7.0 mmol.). The solution was diluted with ether, washed with water, dried (Na$_2$SO$_4$) and evaporated to give the reaction product, which, on filtration through coarse fluorosil (3.5 g.), gave decolorized title compound (0.61 g., 57%), b.p. 96°–98° (0.3 mm), $v_{max}$(film) 1740 cm$^{-1}$, δ(CDCl$_3$) 3.77 (6H,s, 2×CH$_3$), 4.82 (1H,s, —CH), 7.11–7.48 (3H, complex, thienyl protons). C$_9$H$_{10}$O$_4$S requires M,214. Found: M+, 214.

EXAMPLE 19

Preparation of dibenzyl thien-3-ylmalonate

Benzyl 4-trans-2-benzyloxycarbonyl-5-chloro-3-chloro-methyl penta-2,4-dienoate was treated with sodium sulphide as in example 18 thus affording the title compound in 71% yield. Recrystallization from toluene: petrol gave prisms, m.p. 49°–50°, $v_{max}$ (CH$_2$Cl$_2$), 1740 cm$^{-1}$, δ(CDCl$_3$) 4.88 (1H,s, CH), 5.18 (4H,s, 2CH$_2$) 7.33 (13H, complex, aryl and thienyl protons).

EXAMPLE 20

Preparation of ethyl thien-3-ylcyanoacetate

Ethyl 4-Trans-2-cyano-5-chloro-3-chloromethyl penta-2, 4-dianoate was treated with sodium sulphide nonahydrate as in example 18 thus affording the title compound in 30% yield, $v_{max}$ (CH$_2$Cl$_2$) 1720 cm$^{-1}$, δ(CDCl₃) 1.27 (3H,t,J 7 Hz, CH₂), 4.80 (1H,s, CH), 7.2–7.6 (3H, complex, thienyl protons).

EXAMPLE 21

Preparation of methyl thien-3-ylacetate

Potassium hydroxide (0.04 g., 0.06 mmol.) in ethanol (10 ml) at 0° was saturated with H₂S for 15 minutes. Methyl 4-trans-5-chloro-3-choromethyl penta-2,4-dienoate (0.11 g., 0.56 mmol) was added, and the solution stirred with continued H₂S addition for 1 hour. Further potassium hydroxide (0.04 g., 0.6 mmol.) in ethanol (2 ml.) was added. The solution was stirred at room temperature for 18 hours, diluted with water and extracted with ether, which was dried and evaporated to give the title compound (0.07 g.) ν$_{max}$ (CHCl₃) 1730 cm⁻¹, δ (CDCl₃) 3.71 (5H,s, —CH₂— and —CH₃), 7.0–7.6 (3H, complex, thienyl protons), ν$_{max}$(EtOH) 224 (ε4,560), 265 nm (ε2,440). C₇H₈O₂S requires M, 156 Found: M+, 156.

(This compound may also be prepared using preformed sodium bisulphide in place of H₂S/KOH.)

EXAMPLE 22

Preparation of dimethyl thien-3-ylmalonate

Potassium hydroxide (0.14 g, 2.0 mmol) in ethanol (50 ml) was saturated with hydrogen sulphide at 0° C. To this was added methyl-2-methoxycarbonyl-5-chloro-3-chloromethylpenta-2,4-dienoate (0.62 g, 2.45 mmol) and addition of hydrogen sulphide was continued for 1 hour at room temperature. The reaction mixture was stirred for a further 4 hours. Potassium hydroxide (0.20 g, 2.8 mmol) was added and hydrogen sulphide passed for 0.5 hours. The reaction mixture was stirred at room temperature for 16 hours, diluted with water and ether extracted. The extracts were washed with saturated brine, dried and evaporated to give the title compound (0.39 g, 74%), b.p. 96°–98° C./0.3 mm. δ (CDCl₃) 3.77 (6H, s, 2×CH₃), 4.82 (1H, s, CH), 7.11–7.48 (3H, m, thienyl protons). ν$_{max}$ (film) 1740 cm⁻¹ C₉H₁₀O₄S requires M,214. Found: M+, 214.

We claim:

1. Process for the preparation of a thiophene of the formula:

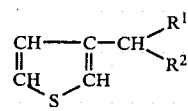

wherein
R¹ is an electron withdrawing group selected from the group consisting of nitrile, the carboxylic acid group and esters and amides thereof, and
R² is hydrogen, alkyl of 1 to 6 carbon atoms, benzyl, phenyl, phenyl substituted with alkyl, naphthyl or the same or different electron withdrawing group as defined for R¹,
which comprises treating a diene of the formula:

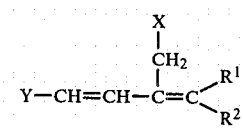

wherein
R¹ and R² are as defined above,
Y is halo, hydroxy or alkoxy, and
X is halo, hydroxy or a functionalized hydroxy group with a source of nucleophilic sulfur in an amount corresponding to at least the molar equivalent amount for said diene and under basic conditions.

2. A process according to claim 1 wherein the source of nucleophilic sulphur is the bisulphide ion.

3. A process according to claim 1 wherein said compound is treated with an alkali metal sulphide.

4. A process according to claim 3 wherein the alkali metal sulphide is sodium sulphide.

5. A process according to claim 1 wherein X and Y are both halo.

6. A process according to claim 5 wherein X and Y are both chloro.

7. A process according to claim 1 wherein R² is hydrogen, a carboxylic acid or ester group.

8. A process according to claim 7 wherein R² is a carboxylic acid group or a carboxylic ester group of formula —CO₂R³, wherein R³ is alkyl of 1 to 6 carbon atoms, benzyl, phthalidyl, indanyl, phenyl, or phenyl substituted with one, two or three alkyl groups each of from 1 to 6 carbon atoms.

9. A process according to claim 1 wherein each of R¹ and R₂ is a carboxylic acid or ester group.

* * * * *